US00PP28002P3

(12) United States Plant Patent
de Wet

(10) Patent No.: US PP28,002 P3
(45) Date of Patent: May 9, 2017

(54) ***ALOE* PLANT NAMED 'SAFARI ROSE'**

(50) Latin Name: ***Aloe* hybrid**
Varietal Denomination: Safari Rose

(71) Applicant: Charles Andrew de Wet, Johannesburg (ZA)

(72) Inventor: Charles Andrew de Wet, Johannesburg (ZA)

( * ) Notice: Subject to any disclaimer, the term of this patent is extended or adjusted under 35 U.S.C. 154(b) by 99 days.

(21) Appl. No.: 14/756,470

(22) Filed: Sep. 8, 2015

(65) Prior Publication Data

US 2016/0249511 P1 Aug. 25, 2016

Related U.S. Application Data

(60) Provisional application No. 62/176,490, filed on Feb. 19, 2015.

(51) Int. Cl.
*A01H 5/00* (2006.01)

(52) U.S. Cl.
USPC ..... Plt./373

(58) Field of Classification Search
USPC ..... Plt./373, 372
CPC ..... A01H 5/02
See application file for complete search history.

*Primary Examiner* — Kent L Bell

(74) *Attorney, Agent, or Firm* — Penny J. Aguirre

(57) ABSTRACT

A new and distinct cultivar of *Aloe* plant named 'Safari Rose', characterized by light salmon-pink colored flowers, medium green-colored foliage tipped with greyed-red, moderately vigorous growth rate, and upright-compact growth habit, is disclosed.

1 Drawing Sheet

Latin name of genus and species of plant claimed: *Aloe* hybrid.

Variety denomination: 'Safari Rose'.

BACKGROUND OF THE INVENTIION

The present invention relates to a new and distinct cultivar of *Aloe* of hybrid origin, botanically known as *Aloe* 'Safari Rose' and will be referred to hereafter by its cultivar name, 'Safari Rose'. 'Safari Rose' is a new cultivar of flowering *Aloe* grown for landscape and container use.

The new cultivar was derived from a controlled breeding program established by the Inventor at a nursery in South Africa in 1973. The overall purpose of the breeding program is to make selections of hybrid *Aloe* with desirable horticultural characteristics to include improved vigor, flowering ability, and disease resistance. 'Safari Rose' was selected in the Inventor's trial bed in June 2007 as a single unique plant from amongst the seedlings derived from a cross made in June 2005 between complex hybrids in the Inventor's breeding program as the female parent and male parents. The female (seed) parent of the new cuitivar is the proprietary *Aloe* hybrid breeding selection uncoded, not patented, characterized by its light white and pink bicolored flowers, light grey-colored foliage, and moderately vigorous, compact growth habit. The male (pollen) parent of the new cultivar is the proprietary *Aloe* hybrid breeding selection coded SP133, not patented, characterized by its light red and white bicolored flowers, light grey-colored foliage, low growth vigor, and upright growth habit.

Asexual reproduction of the new cultivar by offshoots and in vitro propagation since June 2007 in Linbro Park, Republic of South Africa and Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Safari Rose' as a new and distinct cultivar of *Aloe* plant:

1. Light salmon-pink colored flowers;
2. Medium green-colored foliage tipped with greyed-red;
3. Moderately vigorous growth rate; and
4. Upright-compact growth habit.

Plants of the new cultivar differ from its female and male parents primarily in flower and foliage color.

Of the many commercially available *Aloe* cultivars, the most similar in comparison to the new cultivar is Safari Sunrise 'X5', U.S. Plant Pat. No. 23,267. However, in side by side comparisons, plants of the new cultivar differ from plants of 'X5' in at least the following characteristics:

1. Plants of the new cultivar have a flower color different from plants of 'X5';
2. Plants of the new cultivar have a leaf color different from plants of 'X5'; and
3. Plants of the new cultivar have slightly larger flowers than plants of 'X5'.

In addition plants of the new cultivar can be compared to *Aloe* Hedgehog 'Andhopg', not patented. However, in side by side comparisons, plants of the new cultivar differ from plants of 'Andhopg' in at least the following characteristics:

1. Plants of the new cultivar have a flower color different from plants of 'Andhopg';
2. Plants of the new cultivar have a leaf color different from plants of 'Andhopg'; and
3. Plants of the new cultivar are sterile, unlike plants of 'Andhopg'.

BRIEF DESCRIPTION OF THE PHOTOGRAPHS

The accompanying photograph show, as nearly true as it is reasonably possible to make the same in color illustrations of this type, typical flower and foliage characteristics of the new cultivar. Colors in the photograph may differ slightly from the color values cited in the detailed description, which accurately describes the colors of 'Safari Rose'. The plants were 18 months old and grown in 1-gallon containers for 10 months in a poly-covered greenhouse in Arroyo Grande, Calif.

DETAILED BOTANICAL DESCRIPTION

Figure 1:
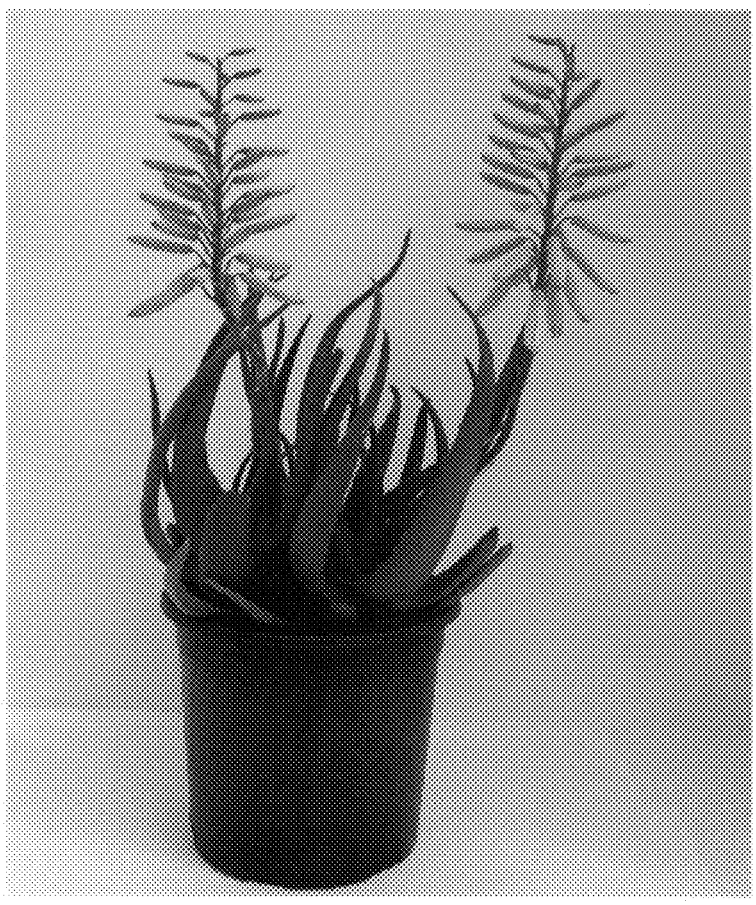
FIG. 1 illustrates a side view of the overall growth and flowering habit of 'Safari Rose'.
Figure 2:
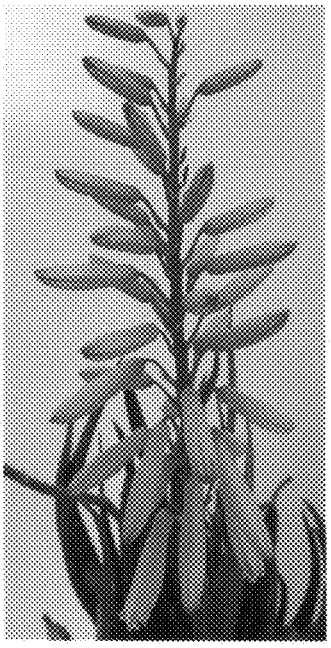
FIG. 2 illustrates a close-up view of an inflorescence of 'Safari Rose'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in West Chicago, Ill.

The following descriptions and measurements describe plants produced from in vitro plantlets from stock plants and grown in a poly-covered greenhouse without supplemental heating or cooling. Temperatures for this period ranged from an average daily high of 71° F. (22° C.) to an average daily low of 50° F. (10° C.). The plants were 18 months old and grown in Arroyo Grande, Calif. in 1-gallon containers for 10 months utilizing a soilless growth medium. No supplemental lighting was provided. Measurements and numerical values represent averages of typical plants.

Botanical classification: *Aloe* hybrid cultivar Safari Rose.

Parentage:

*Female parent.*—Proprietary *Aloe* hybrid breeding selection uncoded, not patented.

*Male parent.*—Proprietary *Aloe* hybrid breeding selection coded SP133, not patented.

Propagation:

*Type.*—Offshoots or in vitro propagules.

*Time required for root development.*—Between 7 to 21 days at an average air temperature of 15° C. to 25° C.

*Time required to develop flowering sized plants.*—9 to 12 months.

*Root description.*—Medium in thickness, fleshy, cream to brown in color.

*Rooting habit.*—Moderately freely branching, dense.

Plant description:

*Plant type.*—*Aloe* hybrid, monoecious, evergreen.

*Plant habit and general appearance.*—Clump forming, rosulate, succulent.

*Blooming habit.*—Blooms autumn to winter and erratically throughout the year in hardy zones.

*Growth rate.*—Moderately vigorous.

*Height and spread.*—Height from soil level to top of plant plane: Approximately 37.0 cm. Width: Approximately 28.0 cm.

*Hardiness.*—U.S.D.A. Zone 10a.

*Diseases and pests.*—No unique aspects concerning susceptibility or resistance.

*Growing conditions.*—Tolerant in a range of soils from humic to sandy to light clay, performs well in full to filtered sun.

*Stems.*—Appearance: Covered by leaf bases. Stem surface: Glabrous. Length: Approximately 6.0 cm. Width at base: Approximately 2.0 cm. Color: 155B.

Foliage description:

*General description.*—Form: Simple. Arrangement: Alternate.

*Leaves.*—Quantity: Approximately 15 per rosette as grown in a 1-gallon container. Shape: Narrowly sword-shaped, elongated. Appearance: Sulcate. Margin: Denticulate, teeth white and tinted 179A in sun. Apex: Tapering to a sharp point. Base: Decurrent. Venation pattern: Parallel. Length: Approximately 21.0 cm. Width: Approximately 3.0 cm. Depth: Approximately 1.0 cm at thickest point. Texture of upper and lower surfaces: Glabrous. Color of upper and lower surfaces: Slightly glaucous 137B with 144A, tipped with 179A, with age tip color becomes 179A to 179B and extends down leaf.

Inflorescence description:

*General description.*—Type: Dense racemes of single flowers held on erect and strong scapes. Length: Approximately 18.0 cm. Width: Approximately 6.0 cm. Fragrance: None detected. Quantity: Approximately 32 flowers and buds per inflorescence, with 1 to 2 inflorescences as grown in a 1-gallon container. Lastingness on plant: Flowers open from base towards the apex, average of 5 days per flower, not persistent.

*Peduncles* (*scapes*).—Strength: Very strong. Length: Approximately 20.0 cm to base of inflorescence. Diameter: Approximately 6.0 mm. Texture: Glabrous. Color: 137A, slightly glaucous.

*Peduncle bracts.*—Arrangement: Alternately along length of peduncle. Shape: Ovate. Apex: Apiculate. Base: Truncate. Length: Approximately 1.0 cm. Width at base: Approximately 6.0 mm. Texture of upper and lower surfaces: Glabrous, papery. Color: Closest to N155D with streaks of 200B.

Flower description:

*General description.*—Type: Solitary, campanulate, not persistent.

*Flower buds just before opening.*—Shape: Cylindrical. Length: Approximately 3.0 cm. Diameter: Approximately 8.0 mm. Texture: Glabrous. Color: 179D with 137A at apex.

*Perianth.*—Length: Approximately 3.2 cm plus pistil extending outward approximately 3.0 mm. Diameter: Approximately 8.0 mm.

*Tepals.*—Quantity: 6, arranged in two whorls. Length: Approximately 3.2 cm. Width: Approximately 5.0 to 6.0 mm, lower 3.0 mm fused. Margin: Entire. Apex: Broadly acute. Base: Fused. Texture of lower (outer) and upper (inner) surfaces: Glabrous. Color of lower (outer) surface when first and fully open: 179D, 179C at base, apex of 155D with a small central vein of 144A. Color of upper (inner) surface when first and fully open: 179D with approximately upper half of 155D and venation of 145A.

*Pedicels.*—Length: Approximately 1.0 cm. Diameter: Approximately 1.0 mm. Texture: Glabrous. Color: 144A tinted with 179A, slightly glaucous.

*Reproductive organs.*—Androcoecium: Stamen quantity: 6 per flower, inserted at base of ovary. Stamen length: Approximately 2.8 cm. Filament length: Approximately 2.7 cm. Filament color: Close to 154D. Anther shape: Bilobed, dorisfixed. Anther length: Approximately 2.0 mm. Anther color: N25A with 25A. Pollen amount: Sparse. Pollen color: 25C. Gynoecium: Pistil quantity: 1 per flower. Pistil length: Approximately 3.5 cm. Stigma shape: Capitate. Stigma length: Less than 1.0 mm. Stigma color: 145D. Style length: Approximately 2.8 cm. Style color: 145C. Ovary shape: Ovoid, superior. Ovary length: Approximately 7.0 mm. Ovary width: 3.0 mm. Color: 144A.

Seed and fruit production: Neither seed nor fruit production has been observed.

What is claimed is:

1. A new and distinct cultivar of *Aloe* plant named 'Safari Rose', substantially as herein illustrated and described.

* * * * *